United States Patent [19]

Stella et al.

[11] Patent Number: 5,376,645

[45] Date of Patent: * Dec. 27, 1994

[54] DERIVATIVES OF CYCLODEXTRINS EXHIBITING ENHANCED AQUEOUS SOLUBILITY AND THE USE THEREOF

[75] Inventors: Valentino J. Stella; Roger Rajewski, both of Lawrence, Kans.

[73] Assignee: University of Kansas, Lawrence, Kans.

[*] Notice: The portion of the term of this patent subsequent to Jul. 28, 2008 has been disclaimed.

[21] Appl. No.: 918,702

[22] Filed: Jul. 27, 1992

Related U.S. Application Data

[63] Continuation-in-part of Ser. No. 469,087, Jan. 23, 1990, Pat. No. 5,134,127.

[51] Int. Cl.$^5$ .................. C08B 37/16; A61K 31/71; A61K 31/715
[52] U.S. Cl. ............................ 514/58; 514/778; 514/964; 514/965; 536/103
[58] Field of Search ............ 536/103; 514/58, 778, 514/964, 965

[56] References Cited

U.S. PATENT DOCUMENTS

| | | | |
|---|---|---|---|
| 3,426,011 | 2/1969 | Parmerter et al. | 536/58 |
| 3,816,393 | 6/1974 | Hayashi et al. | 536/103 |
| 4,497,803 | 2/1985 | Harada et al. | 536/58 |
| 4,535,152 | 8/1985 | Szejtli et al. | 536/103 |
| 4,555,504 | 11/1985 | Jones | 536/103 |
| 4,582,900 | 4/1986 | Brandt et al. | 536/103 |
| 4,596,795 | 6/1986 | Pitha | 536/103 |
| 4,638,058 | 1/1987 | Brandt et al. | 536/103 |
| 4,727,064 | 2/1988 | Pitha | 536/103 |
| 4,746,734 | 5/1988 | Tsuchiyama et al. | 536/103 |
| 4,764,604 | 8/1988 | Mueller | 536/103 |
| 4,774,329 | 9/1988 | Friedman | 536/58 |
| 4,808,232 | 2/1989 | Beesley | 536/58 |
| 4,869,904 | 9/1989 | Uekama et al. | 514/58 |
| 5,134,127 | 7/1992 | Stella et al. | 536/103 |

OTHER PUBLICATIONS

Proceedings Of The Fourth International Symposium On Cyclodextrins (1988) pp. 369-382, "Cyclodextrin Derivatives for Solubilisation, Stabilization and Absorption of Drugs", B. W. Mueller et al.

Third International Symposium On Recent Advances In Drug Delivery Systems (1987) pp. 1-12, "Amorphous Water Soluble Derivatives of Cyclodextrins. From Test Tube to Patient", Josef Pitha.

*Primary Examiner*—Ronald W. Griffin
*Attorney, Agent, or Firm*—Birch, Stewart, Kolasch & Birch

[57] ABSTRACT

Sulfoalkyl ether cyclodextrin derivatives and their use as solubilizing agents for water insoluble drugs for oral, intranasal, or parenteral administration are disclosed.

47 Claims, 10 Drawing Sheets

FIG. I

DERIVATIVES OF CYCLODEXTRINS EXHIBITING ENHANCED AQUEOUS SOLUBILITY AND THE USE THEREOF

This application is a continuation in part of Ser. No. 07/469,087 filed Jan. 23, 1990 now U.S. Pat. No. 5,134,127.

BACKGROUND OF THE INVENTION

1. Field of the Invention

The present invention relates to cyclodextrin derivatives and to their pharmaceutical application as clathrating agents.

2. Discussion of the Background

Cyclodextrins (CD) are a group of cyclic homologous oligosaccharides that are obtained from the degradation of starch by the action of the enzyme cyclodextrin transglycosylase elaborated by the bacterium *Bacillus macerans*. Published methods exist for the production of cyclodextrin transglycosylase as well as making and isolating the cyclodextrins.

Cyclodextrins are cyclic molecules containing six or more α-D-glucopyranose units linked at the 1,4 positions by α linkages as in amylose. As a consequence of this cylic arrangement, the molecule is characterized as having neither a reducing end group nor a non-reducing end group.

The molecule is represented below by schematic formula (1) where the hydroxyl groups are shown in the 2, 3, and 6-positions of the glucopyranose units.

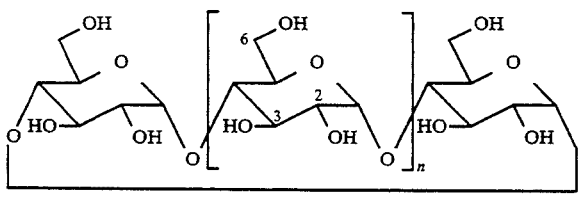

Variable n may be a number from 4 to 6, or higher.

When n=4 the molecule is commonly known as α-cyclodextrin or cyclohexaamylose, when n=5 the molecule is commonly known as β-cyclodextrin or cycloheptaamylose and when n=6 the molecule is commonly known as "-cyclodextrin or cyclooctaamylose. When reference is made here to "cyclodextrin", it is intended to include the foregoing forms of cyclodextrin as well as molecules where n>6.

It is believed that as a consequence of the cylic arrangement and the conformation of the α-D-glucopyranose units, there is limited free rotation about the glycosidic bonds, and the cyclodextrins exist as conical shaped molecules with the primary hydroxyls situated at the small end of the cone and the secondary hydroxyls situated at the large opening to the cone. The cavity is lined by hydrogen atoms from $C_3$ and $C_5$ along with the glucosidic oxygen atoms resulting in a relatively lipophilic cavity but hydrophilic outer surface.

As a result of the two separate polar regions and the changes in solvent structure that occur upon complexation, cyclodextrins have the ability to form complexes with a variety of organic and inorganic molecules. The formation of cyclodextrin inclusion complexes with molecules is referred to as the "host-guest" phenomenon.

These unique properties of cyclodextrins have resulted in their commercial application in agriculture, water treatment, as surfactants and in drug delivery systems. The application of cyclodextrins in the pharmaceutical field has resulted in time release micro encapsulation, improved stability, and increased aqueous solubility of various drugs.

Cyclodextrins are known generally to improve the dissolution rate of drugs. The complexes formed are, however, also stable in aqueous solution, so that the improvement in dissolution is accompanied by an increase in the saturation solubility of the drug. Unfortunately the very β-cyclodextrin that forms the most stable complexes with most drugs has the lowest water solubility, so that drugs that are complexed with it cannot be brought into solution at therapeutic concentrations. The reason for this appears to be due to the crystalline structure of β-cyclodextrin itself.

Chemical modification of cyclodextrins is known to modulate their properties. Electroneutral cyclodextrins have been described by Parmerter et al (U.S. Pat. No. 3,453,259), and Gramera et al (U.S. Pat. No. 3,459,731). These are obtained by the condensation reaction of cyclodextrins with various epoxides or organic halides.

Other derivatives include cyclodextrins with cationic properties (Parmerter (I); U.S. Pat. No. 3,453,257), insoluble crosslinked cyclodextrins (Solms; U.S. Pat. No. 3,420,788), and cyclodextrins with anionic properties (Parmerter (II); U.S. Pat. No. 3,426,011). Among the cyclodextrin derivatives with anionic properties, carboxylic acids, phosphorus acids, phosphinous acids, phosphonic acids, phosphoric acids, thiophosphonic acids, thiophosphinic acids, and sulfonic acids (see Parmerter (II), supra), have been appended to the parent cyclodextrin.

Cyclodextrins have found applications in pharmaceutical delivery systems. As a "host" for "guest" drug molecules, these inclusion (clathrate) complexes have shown increased aqueous solubility for pharmaceuticals with intrinsically low aqueous solubility (Jones; U.S. Pat. No. 4,555,504).

This solubilization results in the improved bioavailability for some drugs. As a clathrate complex some drugs have shown improved chemical stability in aqueous solution (Harada et al; U.S. Pat. No. 4,497,803 and Hayashi et al; U.S. Pat. No. 3,816,394). In addition, cyclodextrins have proved effective in controlling the release of highly water soluble pharmaceuticals (Friedman; U.S. Pat. No. 4,774,329).

Despite this pharmaceutical utility, cyclodextrins are not without their limitations. The use of cyclodextrins in the clinical setting is limited to oral and topical dosage forms as the cyclodextrins exhibit nephrotoxicity upon entering the body unmetabolized. Since mammalian enzymes are specific for the degradation of linear starch molecules, the cyclodextrins remain largely unmetabolized and accumulate, due to their recirculation and readsorption, in the proximal tubule cells.

Cyclodextrins and their derivatives are mostly crystalline solids and concentration in the renal tissue is followed by crystal formation causing necrotic damage to the cells. Despite forming water soluble clathrate complexes, the crystalline cyclodextrin drug complexes have been limited in their utility to sublingual administration.

Efforts have been made to inhibit crystal formation in cyclodextrin drug complexes by derivatizing parent cyclodextrins in a non-specific manner to obtain amorphous mixtures containing many cyclodextrin derivative components (cf. Pitha; U.S. Pat. Nos. 4,596,795 and 4,727,064). These mixtures prevent the crystallization processes seen with single compounds, providing a lowering of toxicity.

SUMMARY OF THE INVENTION

The present invention provides purified cyclodextrin derivatives present both as single derivatives and as mixtures of derivatives. These are obtained by heating a cyclodextrin starting material with a reagent(s) which introduces a specific anionic-type substituent, i.e., a ($C_{2-6}$ alkylene)-$SO_3^-$ anionic substituent, onto the cyclodextrin molecule. These have been discovered to possess notably enhanced aqueous solubility and an advantageously low degree of toxicity. The more highly substituted cyclodextrin derivatives have further been found to advantageously cause essentially no membrane disruption. These derivatized cyclodextrins are useful as clathrating agents in parenteral pharmaceutical formulations and other related uses.

BRIEF DESCRIPTION OF THE FIGURES

A more complete appreciation of this invention and many of its attendant advantages will be readily obtained as the same becomes better understood by the reference to the following detailed description when considered in connection with the accompanying figures, wherein.

DETAILED DESCRIPTION OF THE PREFERRED EMBODIMENTS

Figure 1:
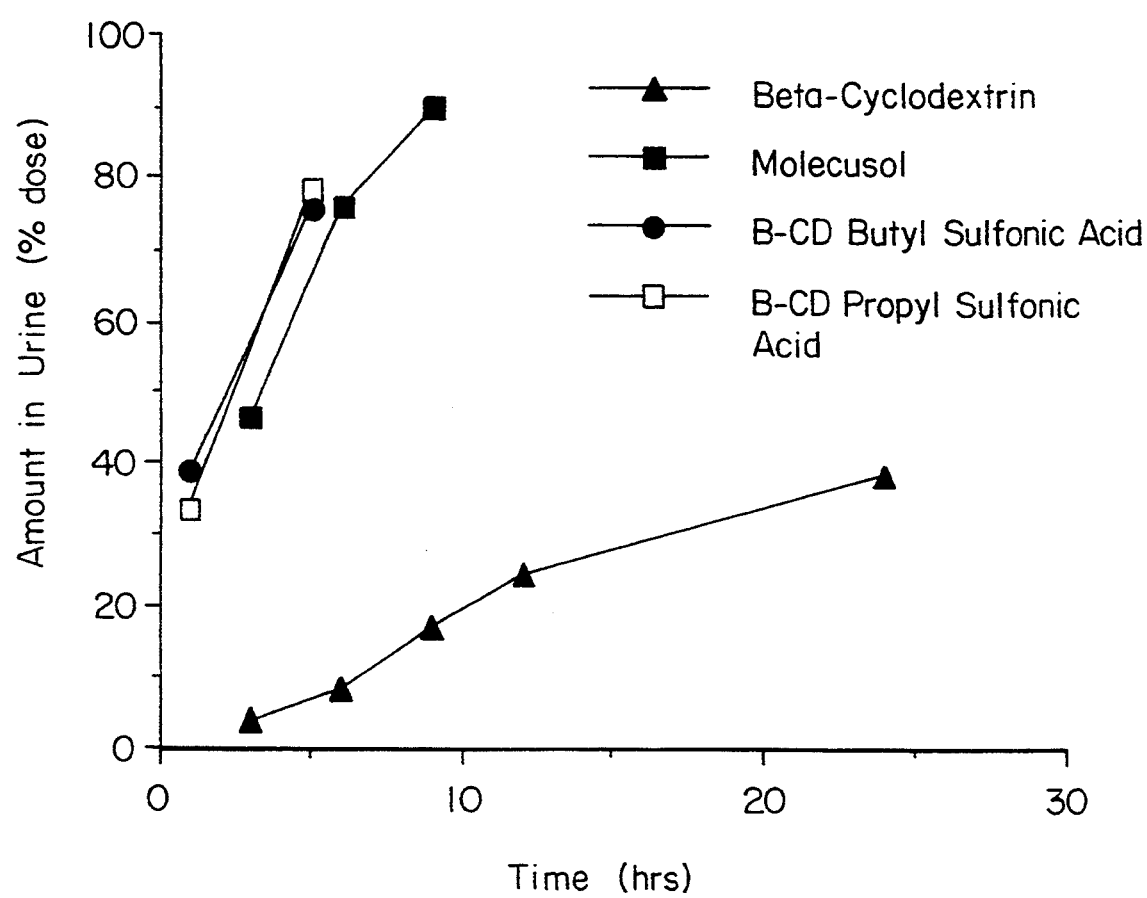
FIG. 1 sets out cumulative urinary cyclodextrin excretion in mice for underivatized cyclodextrin, hydroxy propyl-derivatized cyclodextrin, and two sulfoalkyl cyclodextrin derivatives of the present invention.

Thus this invention provides cyclodextrin derivatives suitable for pharmaceutical use. These derivatives are suitable for use as clathrating agents with drugs to provide clathrate complexes which are useful in parenteral and other pharmaceutical formulations. Procedures for making and isolating the cyclodextrin derivatives are also provided.

The cyclodextrin derivatives of the present invention are functionalized with ($C_{2-6}$alkylene)-$SO_3^-$ groups, and are thus charged species. The fact that these compounds have been discovered to possess a very low level of toxicity is surprising in light of the prior art's belief that cyclodextrin derivatives must retain electroneutrality to sustain lack of toxicity (cf. Pitha, "Amorphous Water-Soluble" "Third Int'l Symposium on Recent Advances in Drug Delivery Systems, Salt Lake City, Utah, Feb. 23-27, 1987).

The high aqueous solubility of the cyclodextrin derivatives of the present invention, and their resulting lowered nephrotoxicity, is further surprising in light of U.S. Pat. No. 4,727,064's disclosure that to maintain a high level of solubility for cyclodextrin derivatives, a mixture of derivatives should be used.

The aqueous solubility exhibited by the present sulfoalkyl cyclodextrin derivatives appears to be obtained through solvation of the sulfonic acid moieties. Thus heterogeneous mixture of the present cyclodextrin derivatives is not a requirement for the observed enhanced solvation to occur. Although a mixture of sulfoalkyl ether derivatives can be used in accordance with the present invention, such a mixture is not required for enhanced solubility.

In a preferred embodiment (1), the cyclodextrin derivatives of this invention have structures represented by formula (2):

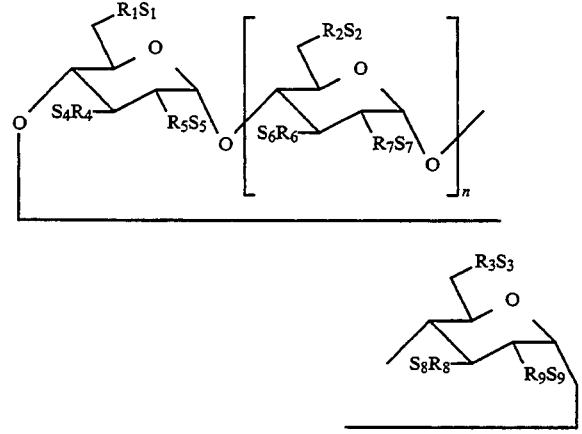

wherein:

n is 4, 5 or 6;

$R_1$, $R_2$, $R_3$, $R_4$, $R_5$, $R_6$, $R_7$, $R_8$ and $R_9$ are each independently, $O^-$ or a O-($C_{2-6}$ alkylene)-$SO_3^-$ group, wherein at least one of $R_1$ and $R_2$ is independently a O-($C_{2-6}$ alkylene)-$SO_3^-$ group, preferably a O-($CH_2$)-$_m SO_3^-$ group, wherein m is 2 to 6, preferably 2 to 4, (e.g. $OCH_2CH_2CH_2SO_3^-$ or $OCH_2CH_2CH_2CH_2SO_3^-$); and $S_1$, $S_2$, $S_3$, $S_4$, $S_5$, $S_6$, $S_7$, $S_8$ and $S_9$ are each, independently, a pharmaceutically acceptable cation which includes, for example, $H^+$, alkali metals (e.g. $Li^+$, $Na^+$, $K^+$), alkaline earth metals (e.g., $Ca^{+2}$, $Mg^{+2}$), ammonium ions and amines cations such as the cations $C_{1-6}$ alkylamines, piperidine, pyrazine, $C_{1-6}$ alkanolamine and $C_{4-8}$ cycloalkanolamine.

In another preferred embodiment (2):

$R_1$ is a O-($C_{2-6}$ alkylene)-$SO_3^-$ group, preferably a O-$(CH_2)$-$_mSO_3^-$ group, (e.g. $OCH_2CH_2CH_2SO_3^-$ or $OCH_2CH_2CH_2CH_2SO_3^-$);

$R_2$ to $R_9$ are $O^-$;

$S_1$ to $S_9$ are as defined in embodiment (1) supra.

In another preferred embodiment (3):

$R_1$, $R_2$ and $R_3$ are each, independently, a O-($C_{2-6}$-alkylene)-$SO_3^-$ group, preferably a O-$(CH_2)_mSO_3^-$ group, (e.g. $OCH_2CH_2CH_2SO_3^-$ or $OCH_2CH_2CH_2CH_2SO_3^-$);

$R_4$ to $R_9$ are $O^-$; and $S_1$ to $S_9$ are as defined in embodiment (1) supra In another preferred embodiment (4):

$R_1$ to $R_3$ are as defined in embodiments (2) or (3); supra;

at least one of $R_4$, $R_6$ and $R_8$ is a O-$C_{2-6}$-alkylene-$SO_3^-$ group, preferably a O-$(CH_2)_mSO_3^-$ group (e.g. $OCH_2CH_2CH_2SO_3^-$ or $OCH_2CH_2CH_2CH_2SO_3^-$).

$R_5$, $R_7$ and $R_9$ are $O^-$; and $S_1$ to $S_9$ are as defined in embodiment (1) supra.

In another preferred embodiment (6):

$R_1$, $R_2$, $R_3$, $R_4$, $R_6$ and $R_8$ are each, independently, a O-($C_{2-6}$-alkylene)-$SO_3^-$ group, preferably a O-$(CH_2)$-$_mSO_3^-$ group (e.g. $OCH_2CH_2CH_2SO_3^-$ or $OCH_2CH_2CH_2CH_2SO_3^-$);

$R_5$, $R_7$ and $R_9$ are $O^-$; and $S_1$ to $S_9$ are as defined in embodiment (1) supra.

The terms "alkylene" and "alkyl" in this text (e.g., in the O-($C_{2-6}$-alkylene)$SO_3^-$ group or in the alkylamines) include both linear and branched, saturated and unsaturated (i.e., containing one double bond) divalent alkylene groups and monovalent alkyl groups, respectively. The term "alkanol" in this text likewise includes both linear and branched, saturated and unsaturated alkyl components of the alkanol groups, in which the hydroxyl groups may be situated at any position on the alkyl moiety. The term "cycloalkanol" includes unsubstituted or substituted (e.g., by methyl or ethyl) cyclic alcohols.

The present invention provides compositions containing a mixture of cyclodextrin derivatives having the structure set out in formula (2), where the composition overall contains on the average at least 1 and up to $3n+6$ alkylsulfonic acid moieties per cyclodextrin molecule. The present invention also provides compositions containing essentially only one single type of cyclodextrin derivative.

The present cyclodextrin derivatives are either substituted at least at one of the primary hydroxyl group (i.e., at least one of $R_1$ to $R_3$ is a substituent), or they are substituted at both the primary hydroxyl group and at the 3-position hydroxyl group (i.e., both at least one of $R_1$ to $R_3$ and at least one of $R_4$, $R_6$ and $R_8$ are a substituent). Substitution at the 2-position hydroxyl group, while theoretically possible, on the basis of the inventors' studies, does not appear to appear to be substantial in the products of the invention.

The cyclodextrin derivatives of the present invention are obtained (as discussed below) as purified compositions, preferably as compositions containing at least 95 wt. % of cyclodextrin derivative(s) with the substitution occuring at least on the primary hydroxyl group of the cyclodextrin molecule (i.e. $R_1$, $R_2$ or $R_3$ of formula (2)), as determined by 300 MHz $^1H$ NMR. In a preferred embodiment, purified compositions containing at least 98 wt. % cyclodextrin derivative(s) can be obtained.

This is to be contrasted with the U.S. Pat. No. 3,426,011 disclosure which reports obtaining only reaction products of the reaction of a cyclodextrin with a sultone reactant. These reaction products contain considerable quantities of unsubstituted cyclodextrin starting material.

In these preferred compositions of the invention unreacted cyclodextrin has been substantially removed, with the remaining impurities (i.e., $\leq 5$ wt. % of composition) being inconsequential to the performance of the cyclodextrin derivative-containing composition.

The more highly substituted alkyl sulfonic acid cyclodextrin derivatives of the present invention have been discovered to possess, in addition to notably enhanced solubility characteristics and low toxicity, the advantageous property of causing less membrane disruption. In red blood cell hemolysis studies, the more highly substituted cyclodextrin derivatives demonstrated negligible membrane disruption. The mono-substituted cyclodextrin derivatives caused about the same amount of membrane disruption as the hydroxy propyl derivative.

These improved characteristics are achieved by the purified compositions of the invention which contain $<5\%$, preferably less than 2%, of unreacted $\beta$-cyclodextrin, and are particularly important for compositions to be administered to a patient by parenteral administration. The present inventors, however, have found that compositions containing somewhat higher amounts of unreacted $\beta$-cyclodextrin, while not suitable for parenteral administration, are still useful for oral administration.

The administration of a drug included into a cyclodextrin preparation by an intravenous route must not contain $\beta$-cyclodextrin due to its inherent nephrotoxicity. An IV administered dose gains access to the kidneys via the route of blood circulation. Once $\beta$-cyclodextrin is filtered by the kidney cells it appears to cause nephrotoxicity due to disruption of cellular membranes caused by removal of cholesterol from the cell membranes. Consequently, there is little tolerance for a derivatized cyclodextrin containing residual $\beta$-cyclodextrin if that product is to be used in a parenteral formulation.

In contrast, the allowance for residual $\beta$-cyclodextrin would be broader for a sulfoalkylether cyclodextrin preparation used in an oral formulation. The oral absorption of $\beta$-cyclodextrin is limited (if it occurs at all) and the elimination of $\beta$-cyclodextrin in the feces would preclude any nephrotoxicity. However, the level of $\beta$-cyclodextrin which might be tolerated in an oral formulation would still be dependent upon other characteristics of the material particularly on its intrinsic aqueous solubility.

As a result, the sulfoalkylether derivatives of the present invention may be used for oral formulations, even if unreacted $\beta$-cyclodextrin is contained in an amount of up to about 50%, although preferably the amount is limited to less than 40%, and most preferably less than about 25%.

Preparation of the Cyclodextrin (CD) Derivatives:

The cyclodextrin derivatives described may be generally prepared by dissolving the cyclodextrin in aqueous base at an appropriate temperature, e.g., 70° to 80° C., at the highest concentration possible. For example, to prepare the cyclodextrin derivatives of embodiment (4), an amount of an appropriate alkyl sultone, corresponding to the number of moles of primary CD hydroxyl group present, is added with vigorous stirring to ensure maximal contact of the heterogeneous phase.

To prepare the cyclodextrin derivatives of the embodiment (2) a molar amount of the alkyl sultone, corresponding to the number of moles of CD used, is used. As would be readily determinable by one of skill in this art, to prepare cyclodextrin derivatives of embodiment (1), which encompasses both cyclodextrin derivatives embodiments (4) and (2), an amount of alkyl sultone between that stated above is used. Other cyclodextrin derivatives provided by the present invention are prepared Mutatis Mutandis.

The mixtures are allowed to react until one phase results which is indicative of depletion of the alkyl sultone. The reaction mixture is diluted with an equal volume of water and neutralized with an acid such as hydrochloric acid. The solution is then dialyzed to remove impurities followed by concentration of the solution by ultrafiltration.

The concentrated solution is then subjected to ion-exchange chromatography to remove unreacted cyclodextrin, and then freeze-dried to yield the desired product.

The CD used in this invention may be any CD obtained by known methods, e.g., by the action of cyclodextrin-glucanotransferase (CGTase, E.C., 2.4.1.19.) upon starch. Thus CD herein means $\alpha$-CD in which six glucose units are linked together through $\alpha$-1,4 bond, $\beta$-CD in which seven glucose units are linked together, or $\gamma$-CD in which eight glucose units are linked together, or a mixture thereof. Of these, use of $\beta$-CD is most preferred for production of partially derivatized products of broad utility.

As noted above and depending on the cyclodextrin derivative sought, the amount of alkyl sultone used as the derivatizing agent should be not more than about one molar equivalent, based on the number of primary hydroxyl groups present in the CD, although the optimum amount may be somewhat dependent on the reactant concentration. Lithium hydroxide, sodium hydroxide and potassium hydroxide may be used as the accelerator. Of these, sodium hydroxide is preferable because of the its low cost. Its amount must be more than about 30 molar equivalents, and should preferably be in the range of 80 to 200 molar equivalents, with the reactant concentration being set at a level higher than 10% (wt/wt), preferably in the range of 40 to 60% (wt/wt).

Any solvent which is substantially inert to the partial alkylation may be used as reaction medium. Typical examples are water, DMF, DMSO, and mixtures thereof, but use of water alone is most preferred for ease of after-treatment.

The type and concentration of alkylsultone and alkali are not critical to the reaction. However, the reaction is normally carried out with stirring at 10° to 80° C. for one hour, preferably at 20° to 50° C. for 5 to 20 hours.

Techniques commonly used in this field may be employed to isolate and purify the objective compounds from reaction mixtures. These include extraction with organic solvents, dialysis, adsorption chromatography with activated charcoal, silica gel, alumina and other adsorbents, chromatography using, as carrier, cross-linked dextrin, styrene/divinylbenzene copolymers and other cross-linked polymers, and combinations thereof.
Preparation of the Clathrate Complexes:

The clathrate complexes of the invention may be prepared by any method known in the art for the preparation of complexes of cyclodextrins.

For example, to prepare the clathrate complexes, a cyclodextrin derivative dissolved in water or in an organic solvent miscible with water may be added to a physiologically active compound (drug) dissolved in an organic solvent which is miscible with water. After the mixture is heated, the desired product is obtained by concentrating the mixture under reduced pressure or leaving it to be cooled. In this case, the mixing ratio of organic solvent with water may be suitably varied according to the solubilities of the starting materials and products.

Examples of drugs which may be complexed with the cyclodextrin derivatives include diphenyl hydantoin, adiphenine, allobarbital, aminobenzoic acid, amobarbital, ampicillin, anethole, aspirin, azopropazone, azulene barbituric acid, beclomethasone, beclomethasone dipropronate, bencyclane, banzaldehyde, benzocaine, benzodiazepines, benzothiazide, betamethasone, betamethasone 17-valerate, bromobenzoic acid, bromoisovalerylurea, butyl-p-aminobenzoate, chloralhydrate, chlorambucil, chloramphenicol, chlorobenzoic acid, chlorpromazine, cinnamic acid, clofibrate, coenzyme A, cortisone, cortisone acetate, cyclobarbital, cyclohexyl anthranilate, deoxycholic acid, dexamethasone, dexamethasone acetate, diazepam, digitoxin, digoxin, estradiol, flufenamic acid, fluocinolone acetonide, 5-fluorouracil, flurbiprofen, griseofulvin, guaiazulene, hydrocortisone, hydrocortisone acetate, ibuprofen, indican, indomethacin, iodine, ketoprofen, lankacidin-group antibiotics, mefanamic acid, menadione, mephorbarbital, methbarbital, methicillin, metronidazole, mitomycin, nitrazepam' nitroglycerin' nitrosureas, paramethasone, penicillin, pentobarbital, phenobarbital, phenobarbitone, phenyl-butyric acid, phenyl-valeric acid, phenytoin, prednisolone, prednisolone acetate, progesterone, propylparaben, proscillaridin, prostaglandin A series, prostaglandin B series, prostaglandin E series, prostaglandin F series, quinolone antimicrobials, reserpine, spironolactone, sulfacetamide sodium, sulphonamide, testosterone, thalidomide, thiamine dilaurylsulphate, thiamphenicol-palmitate, thiopental, triamcinolone, vitamin A, vitamin D3, vitamin E, vitamin K3, and warfarin.

The drug may be dissolved in water or an organic solvent (either miscible or immiscible with water). Convenient solvents include for example diethylether, tetrahydrofuran, dioxane, acetone, dimethylsulfoxide, dimethylformamide and lower aliphatic alcohols. Preferably the drug is dissolved in either water or a mixture of water and a water-miscible solvent such as methanol or ethanol. The drug may also be suspended in water.

After equilibrium is reached, the complex may be isolated by any suitable technique for example lyophilization, evaporation of the solvent, precipitation, low temperature crystallization, or spray-drying. Cyclodextrin inclusion complexes may also be produced by physicially grinding or kneading the cyclodextrin and the guest molecule with or without a small amount of solvent.

The ratio of cyclodextrin derivative to drug used to prepare the clathrate complexes of the invention may be any convenient ratio but conveniently the cyclodextrin derivative is used in a molar excess.

The benefits derived from the invention may be obtained by having the molar ratio of cyclodextrin derivative to drug in the range of 10:1 to 1:10 preferably 2:1 to 5:1 for example 3:1 and by using the methods and ratios described above. Complexes are conveniently obtained containing up to 20% w/w of the drug. However in view of the low doses of the drug normally administered and the difficulty of preparing homogenous mixtures of active ingredient and excipients it may be desirable to prepare the complex with an excess of the cyclodextrin derivative present, for example complexes containing in the order of 0.1 to 10% by weight of the drug, particularly in the range 0.5 to 0.2% by weight.

The clathrate complexes of the invention provide a more convenient way of administering the drugs, the cyclodextrin acting merely as a solubilizing agent without altering the therapeutic behavior of the drug in any way.

Composition Containing the Clathrate Complexes of the Invention:

The invention thus also provides an inclusion complex as defined herein for use in human or veterinary medicine. The complex, for use as a pharmaceutical, may presented as a pharmaceutical formulation.

The invention therefore provides in a further aspect a pharmaceutical formulation comprising an inclusion complex of a drug with a cyclodextrin derivative together with a pharmaceutically acceptable carrier therefore and optionally other therapeutic and/or prophylactic ingredients. The carriers must be "acceptable" in the sense of being compatible with the other ingredients of the formula and not deleterious to the recipient thereof. Suitably the pharmaceutical formulation will be in unit dosage form. Each unit dose will conveniently contain that amount of drug normally incorporated into a unit dose of such drug in the absence of a cyclodextrin.

The pharmaceutical formulations may be any formulation in which the inclusion complexes may be administered and include those suitable for oral, intranasal, intraoccular or parenteral (including intramuscular and intravenous) administration. The formulations may, where appropriate, be conveniently presented in discrete dosage units and may be prepared by any of the methods well known in the art of pharmacy. All methods include the step of bringing into association the active compound with liquid carriers or finely divided solid carriers or both, and then, if necessary, shaping the product into the desired formulation.

Pharmaceutical formulations suitable for oral administration wherein the carrier is a solid are most preferably presented as unit dose formulations such as boluses, capsules, cachets or tablets each containing a predetermined amount of the active ingredient. A tablet may be made by compression or molding, optionally with one or more accessory ingredients. Compressed tablets may be prepared by compressing in a suitable machine the active compound in a free-flowing form such as a powder or granules optionally mixed with a binder, lubricant, inert diluent, lubricating, surface active or dispersing agent. Molded tablets may be made by molding an inert liquid diluent. Tablets may be optionally coated and, if uncoated, may optionally be scored. Capsules may be prepared by filling the active compound, either alone or in admixture with one or more accessory ingredients, into the capsule cases and then sealing them in the usual manner. Cachets are analogous to capsules wherein the active ingredient together with any accessory ingredient(s) is sealed in a rice paper envelope.

Tablets contain the active ingredient in admixture with non-toxic pharmaceutically acceptable excipients which are suitable for manufacture of tablets. These excipients may be, for example, inert diluents, such as calcium carbonate, sodium carbonate, lactose, calcium phosphate or sodium phosphate; granulating and disintegrating agents, for example maize starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate alone or with a wax may be employed.

The present invention also provides the complexes of the present invention in pharmaceutical formulations exhibiting sustained release of a drug. Pharmaceutical formulations exhibiting sustained release of a drug are generally known. Such formulations include devices made of inert polymers or biodegradable poly-acids in which the active ingredient (the present complex) is either dispersed, covalently linked via labile bonds, or stored as a reservoir between polymer membranes. Sustained release is achieved through diffusion of the active ingredient through the polymer matrix or hydrolysis of any covalent linkages present.

Sustained release may also be presented by delivery of the active ingredient via osmotic pumps. Osmotic pumps consist of a reservoir of solution or suspension of active ingredient (i.e., the present complex) surrounded by a semipermeable membrane containing a drug portal. As water penetrates through the semipermeable membrane into the complex reservoir, the complex solution is pushed through the portal and released.

The cyclodextrin derivatives of the invention act as drug solubilizing agents in these systems. The present cyclodextrin derivatives can also act as osmotic driving agents providing potential for the influx of water in such systems.

Pharmaceutical formulations suitable for oral administration wherein the carrier is liquid may conveniently be presented as a solution in an aqueous liquid or a non-aqueous liquid, or as an oil-in-water or water-in-oil liquid emulsion. Pharmaceutical formulations suitable for parenteral administration are conveniently presented in unit dose or multi-dose containers which are sealed after introduction of the formulation unit required for use.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, for example arachis oil, peanut oil, liquid paraffin or olive oil.

It should be understood that in addition to the aforementioned carrier ingredients, the pharmaceutical formulations described above may include, as appropriate, one or more additional carrier ingredients such as diluents, buffers, flavoring agents, binders, surface active agents, thickeners, lubricants, preservatives (including anti-oxidants) and the like, and substances included for the purpose of rendering the formulation isotonic with the blood of the intended recipient.

For these purposes the compounds of the present invention may be administered orally, topically, intranasally, intraoccularly, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally occuring phosphatide, for example, lecithin, or condensation products of an alkylene oxide with fatty acids, for example of polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan mono-oleate. The aqueous suspensions may also contain one or more preservatives, for example, ethyl or n-propyl p-hydroxy benzoate, one or more coloring agents, one or more flavoring agents and one or more sweetening agents, such as sucrose or saccharin.

Oily suspensions may be formulated by suspending the active ingredient in a vegetable oil, for example arachIs oil, olive oil, sesame oil or coconut oil, or in a mineral oil such as liquid paraffin. The oil suspensions may contain a thickening agent, for example beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soya bean lecithin, and esters or partial esters derived from fatty acids and hexitol anhydrides, for example sorbitan mono-oleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and colorinq agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc. containing the active ingredient are employed.

The amount of active ingredient that may be combined with the carrier materials to produce a single dosage form will vary depending upon the host treated and the particular mode of administration. For example, a formulation intended for the oral administration of humans may contain from 1.0 to 750 mg. of active agent compounded with an appropriate and convenient amount of carrier material which may vary vary from about 5 to about 95 weight percent of the total composition. Unit dosage forms will generally contain between from about 1 to about 500 mg. of active ingredient.

Administration of the Clathrate Complexes to a Patient:

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Pharmaceutical formulations containing inclusion complexes may be administered at dosage levels and dosage intervals required to achieve the desired pharmacologic response normally associated with the drug and the disease state in absence of the cyclodextrin.

The other features of the invention will become apparent in the course of the following descriptions of exemplary embodiments which are given for illustration of the invention and are not intended to be limiting thereof.

EXAMPLES

The hydroxypropyl cyclodextrin derivative used in the experiments reported below was purchased from Pharmatec, Inc., Alachua, Fla.

Preparation of the Cyclodextrin Derivative of the Invention

Example 1: Mono-sulfobutyl ether of β-cyclodextrin

In a 100 mL round-bottom flask, 10 grams β-cyclodextrin ($8.81 \times 10^{-3}$ mole) was added with stirring to an aqueous solution composed of 30 mL water and 5.0 grams sodium hydroxide maintained at 70° C. To this solution 1.8 mL (2.40 gm, $1.76 \times 10^{-2}$ mole) butane sultone was slowly added with vigorous stirring to insure maximal contact of the heterogenous phases.

derivatives with varying degrees of substitution. Representative results follow:

| Cyclodextrin | Moles | Sultone | Moles | Carbon/Sulfur Ratio | Substitutions |
| --- | --- | --- | --- | --- | --- |
| β- | $4.41 \times 10^{-3}$ | propane | $4.4 \times 10^{-2}$ | 3.28 | 7.2 |
| β- | $4.41 \times 10^{-3}$ | propane | $2.2 \times 10^{-2}$ | 5.53 | 3.6 |
| β- | $4.41 \times 10^{-3}$ | butane | $2.2 \times 10^{-2}$ | 4.83 | 4.7 |
| γ- | $1.54 \times 10^{-3}$ | propane | $7.71 \times 10^{-3}$ | * | 3.5 |
| γ- | $1.54 \times 10^{-3}$ | butane | $7.71 \times 10^{-3}$ | * | 3.2 |

*Substitution determined by peak areas from $^1$H-NMR spectra.

After a single phase was observed indicating depletion of the alkyl sultone, the solution was cooled to room temperature and diluted with 20 mL water. The resulting solution was neutralized with 1N hydrochloric acid and dialyzed against $3 \times 700$ mL water to remove salts and hydroxyalkyl sufonic acids formed as side products.

The diasylate was concentrated by ultrafiltration and placed on an ion-exchange column composed of 50 grams A-25 DEAE-Sephadex packed in a 1.25 inch i.d. glass column. Unreacted β-cyclodextrin was removed by elution with distilled water. The mono-substituted sulfobutyl ether of β-cyclodextrin was isolated by elution with 0.1N sodium hydroxide. The effluent fraction containing the mono-substituted derivative was ultrafiltered to remove any residual salts. The pH of the retentate was adjusted to neutrality and lyophilized to obtain 2.17 grams of the monosubstituted sulfobutyl ether of β-cyclodextrin as a white amorphous solid. Elemental analysis of the product showed a carbon to sulfur ratio of 13.7 which corresponds to Ca. 1.2 substitutions per molecule.

Example 2: Mono-sulfopropyl ether of β-cyclodextrin

The processes of Example 1 were repeated substituting 1.54 mL (2.15 grams, $1.76 \times 10^{-2}$ mole) propane sultone for butane sultone to yield 1.97 grams mono-sulfobutyl ether of β-cyclodextrin as a white amorphous solid. Elemental analysis of the product showed a carbon to sulfur ratio of 12.1 which corresponds to Ca. 1.4 substitutions per molecule.

Example 3: Sulfobutyl ethers of β-cyclodextrin

In a 50 mL round-bottom flask, 5 grams β-cyclodextrin ($4.41 \times 10^{-3}$ mole) was added with stirring to an aqueous solution composed of 10 mL water and 2.0 grams sodium hydroxide maintained at 70° C. To this solution 4.5 mL (6.0 gm, $4.41 \times 10^{-2}$ mole) butane sultone was slowly added with vigorous stirring to insure maximal contact of the heterogenous phases. After a single phase was observed indicating depletion of the alkyl sultone, the solution was cooled to room temperature and diluted with 20 mL water. The resulting solution was neutralized with 1N hydrochloric acid and dialyzed against $3 \times 700$ mL water to remove salts and hydroxyalkyl sulfonic acids formed as side products. The diasylate was concentrated by ultrafiltration and the pH of the retentate was adjusted to neutrality and lyophilized to obtain the sulfobutyl ether of β-cyclodextrin as a white amorphous solid. Elemental analysis of the product showed a carbon to sulfur ratio of 3.73 which corresponds to Ca. 7 substitutions per molecule. Thin-layer chromatography of the product (2-butanone:methanol:water, 4:4:2) shows the absence of unreacted β-cyclodextrin.

Example 4: Additional sulfoalkylethers of cyclodextrin

The processes of Example 3 were varied with regard to reactants and molar ratios to obtain cyclodextrin Cumulative Urinary Cyclodextrin Excretion:

The data provided in the group set out in FIG. 1 indicates that although the sulfoalkyl cyclodextrin derivatives of the invention well as the hydroxypropyl derivative are excreted faster and to a greater extent in mice than the parent compound, the present derivatives are excreted fastest. FIG. 1 provides data for the underivatized cyclodextrin compound, the hydroxypropyl derivative, the sulfobutyl derivative of the invention, and the sulfopropyl derivative of the invention.

Acute Parenteral Toxicity:

The sulfoalkyl cyclodextrin derivatives of the invention exhibited no observable toxic effects in male mice over a 30 day period following intraperitoneal of $5.49 \times 10^{-3}$ mol/Kg.

This dose is equivalent to 7.1 gm/Kg for the mono-sulfoalkyl derivatives, 12.3 gm/Kg for the sulfobutyl derivative w/7 degrees of substitution, and 11.8 gm/Kg for the sulfopropyl derivative w/7 degrees of substitution.

Plasma Urea Nitrogen:

Plasma urea nitrogen levels are an indicator of kidney function with higher levels indicating renal damage. The data in Table 1 indicates that the sulfoalkyl cyclodextrin derivatives of the invention do not cause increased plasma urea nitrogen levels in mice as compared to the underivatized parent compound (control). There is however no statistical difference between our derivatives and the hydroxypropyl derivative.

TABLE 1

| Plasma Urea Nitrogen[1] | | |
| --- | --- | --- |
| | Sample time (hrs) | PUN + S.D. (mg/dL)[2] |
| Control (normal saline) | 24 | 15.88 ± 1.21 |
| β-Cyclodextrin | 24 | 160.10 ± 26.16 |
| Molecusol ™ (hydroxylpropyl derivative) | 24 | 15.43 ± 1.50 |
| Sulfopropyl ether of β-Cyclodextrin (3.6 substitution per CD molecule) | 24 | 15.27 ± 0.71 |
| Sulfobutyl ether of β-Cyclodextrin (4.7 substitution per CD molecule) | 24 | 14.42 ± 0.46 |

[1]SIGMA Urea Nitrogen Procedure No. 640-A
[2]n = 4

Figure 2:
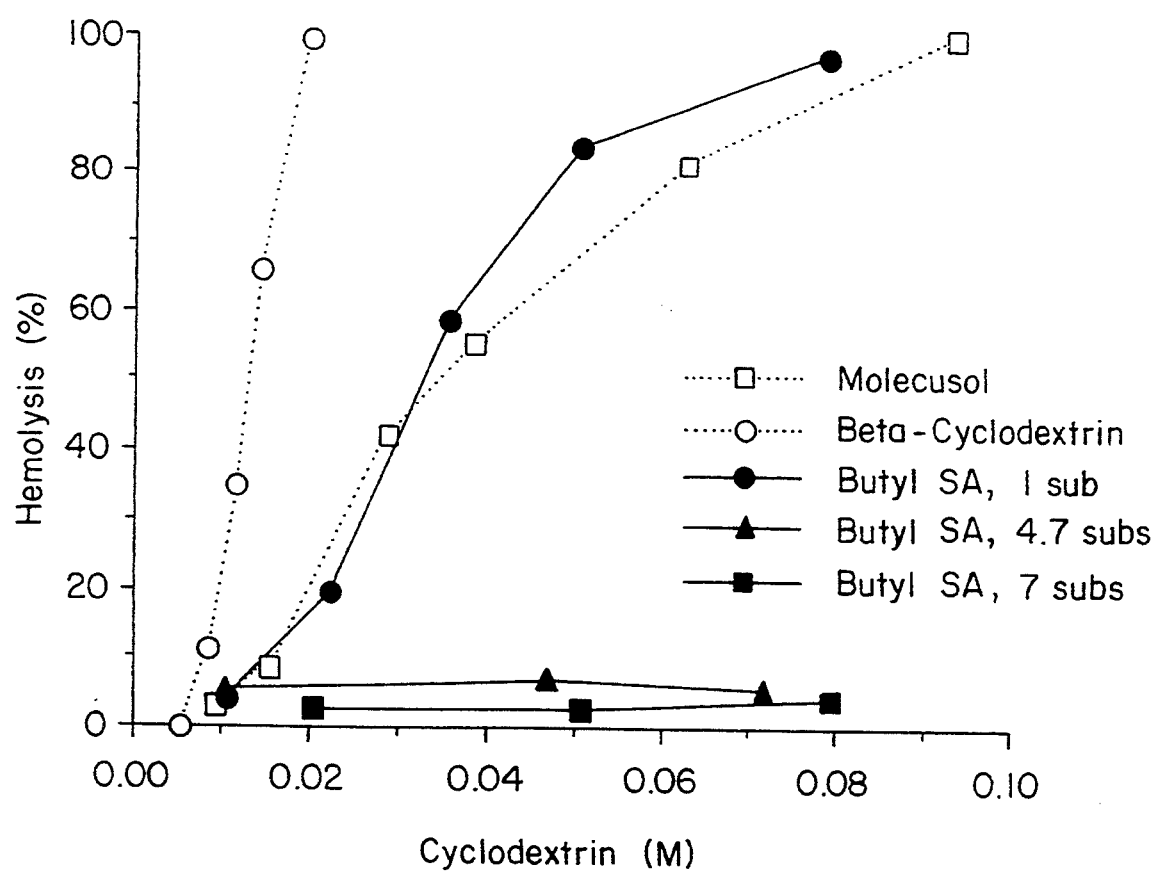
FIGS. 2 and 3 provide data showing that the more highly substituted alkylsulfonic acids of the present invention (butyl and propyl, respectively) cause less membrane disruption, as determined by red blood cell hemolysis studies, as compared to the mono-substituted alkylsulfonic acid derivatives, with the underivatized cyclodextrin causing the most membrane disruption, and that the mono-substituted alkylsulfonic acid derivatives of the present invention cause about the same amount of membrane disruption as does the hydroxypropyl cyclodextrin derivative, as also determined by red blood cell hemolysis study.
Figure 3:
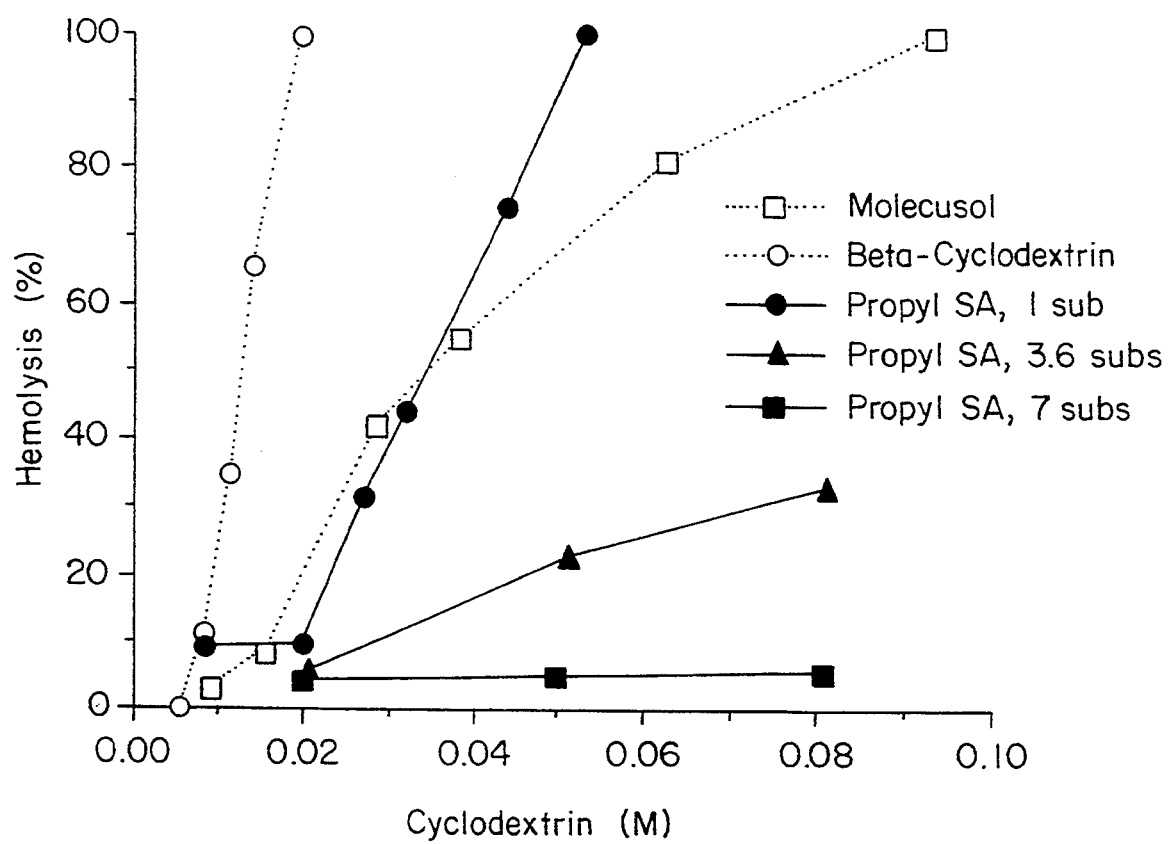

Hemolysis of Red Blood Cells:

As can be seen from the data in FIGS. 2 and 3 the more highly substituted alkylsulfonic acid derivatives of the invention caused less membrane disruption as indicated by the percent hemolysis than the mono substituted derivatives. The mono substituted derivatives caused about the same amount of membrane disruption as the hydroxypropyl derivative.

Figure 4A:
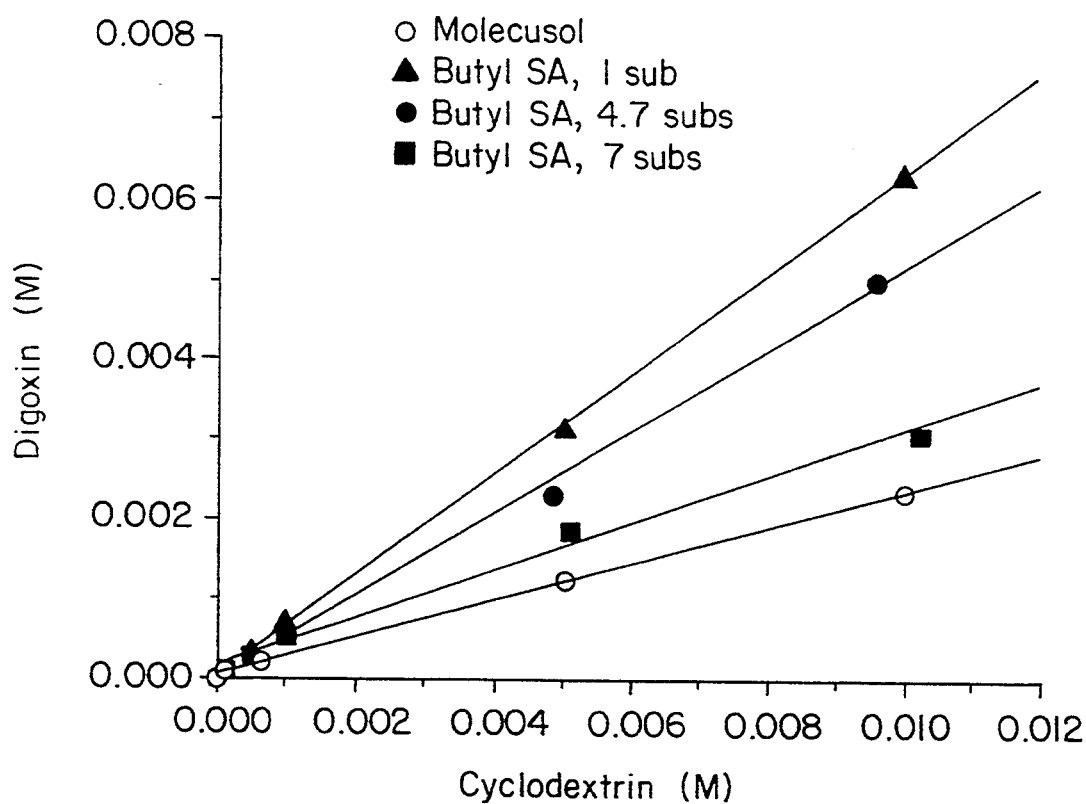
FIGS. 4A, 4B, 5 and 6 show that the association constants for the equilibrium between the sulfoalkyl cyclodextrin derivatives of the present invention and digoxin or progesterone are considerably larger than the association constant for the equilibrium between a hydroxypropyl cyclodextrin derivative and digoxin or progesterone, respectively.
Figure 4B:
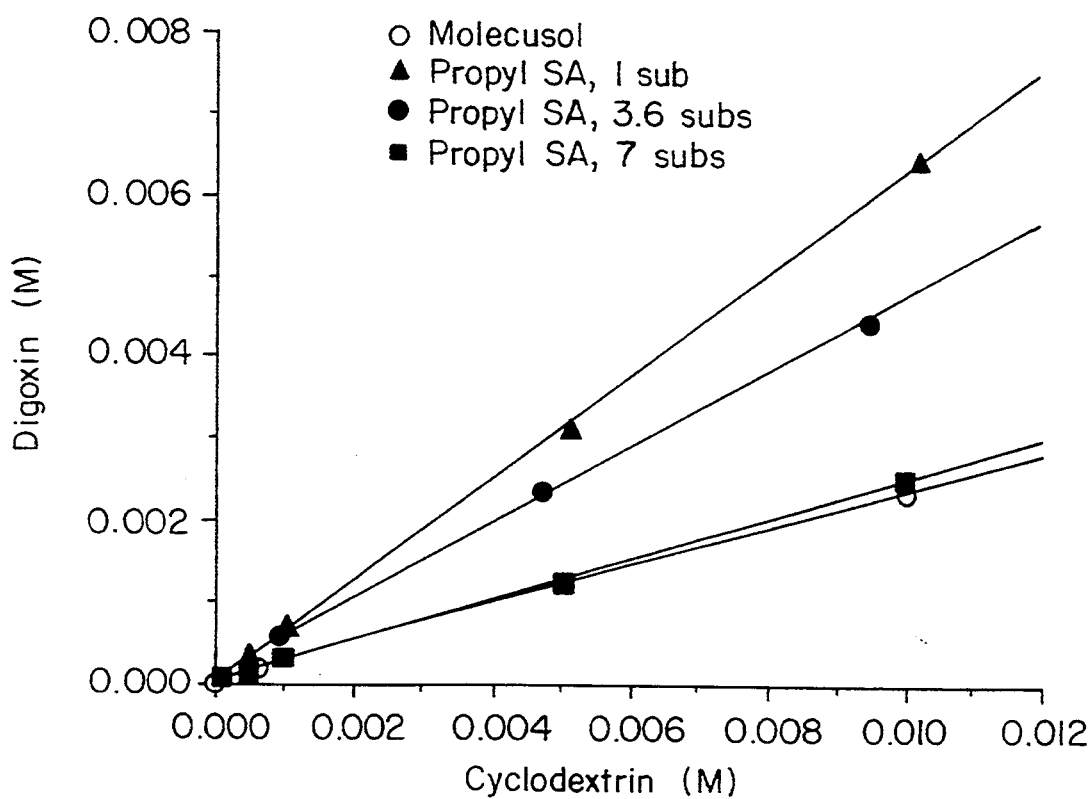

Phase Solubility Behavior:

As can be seen from Table 2 below and the data provided in FIGS. 4A and 4B the association constants for the equilibrium between the sulfobutyl derivatives of the invention and Digoxin (FIG. 4A) are 5 times larger than that of the hydroxypropyl derivatives (FIG. 4B).

TABLE 2
DIGOXIN ASSOCIATION CONSTANTS

| | $K_{1:1}(M^{-1})$ |
|---|---|
| β-Cyclodextrin | $2.82 \times 10^4$ |
| Molecusol (hydroxypropyl-β-C) | $4.90 \times 10^3$ |
| Sulfobutyl ether of β-cyclodextrin | |
| (1 sub)[1] | $2.76 \times 10^4$ |
| (4.8 subs) | $1.71 \times 10^4$ |
| (7 subs) | $6.88 \times 10^3$ |
| Sulfopropyl ether of β-cyclodextrin | |
| (1 sub) | $2.74 \times 10^4$ |
| (3.6 subs) | $1.41 \times 10^4$ |
| (7 subs) | $5.29 \times 10^3$ |

[1]No. of substituents per CD molecule

TABLE 3
PROGESTERONE ASSOCIATION CONSTANTS

| | $K_{1:1}(M^{-1})$ |
|---|---|
| β-cyclodextrin | — |
| Molecusol (hydroxypropyl β-CD) | $1.12 \times 10^4$ |
| Sulfobutyl ether β-cyclodextrin | |
| (1 sub)[1] | $1.72 \times 10^4$ |
| (4.7 subs) | $1.57 \times 10^4$ |
| (7 subs) | $1.83 \times 10^4$ |
| Sulfopropyl ether β-cyclodextrin | |
| (1 sub) | $1.66 \times 10^4$ |
| (3.6 subs) | $1.19 \times 10^4$ |
| (7 subs) | $7.68 \times 10^3$ |

[1]No. of substituents per CD molecule

It should be noted that the x axis for the graphs of FIGS. 4A and 4B have a maximum of ~1.8% w/w cyclodextrin. If the relative solubilizing ability of the present derivatives is considered relative to that for the hydroxypropyl derivative (at 50% solutions as is done in U.S. Pat. No. 4,727,064, Table 1) the apparent solubility of digoxin is ~216 mg/mL for the present sulfobutyl derivatives as compared to ~80 mg/mL for the hydroxypropyl derivative. The value of 45.0 mg/mL reported in U.S. Pat. No. 4,727,064 was for a hydroxypropyl derivative with a different degree of substitution than the hydroxypropyl derivative used herein for comparison.

Figure 5:
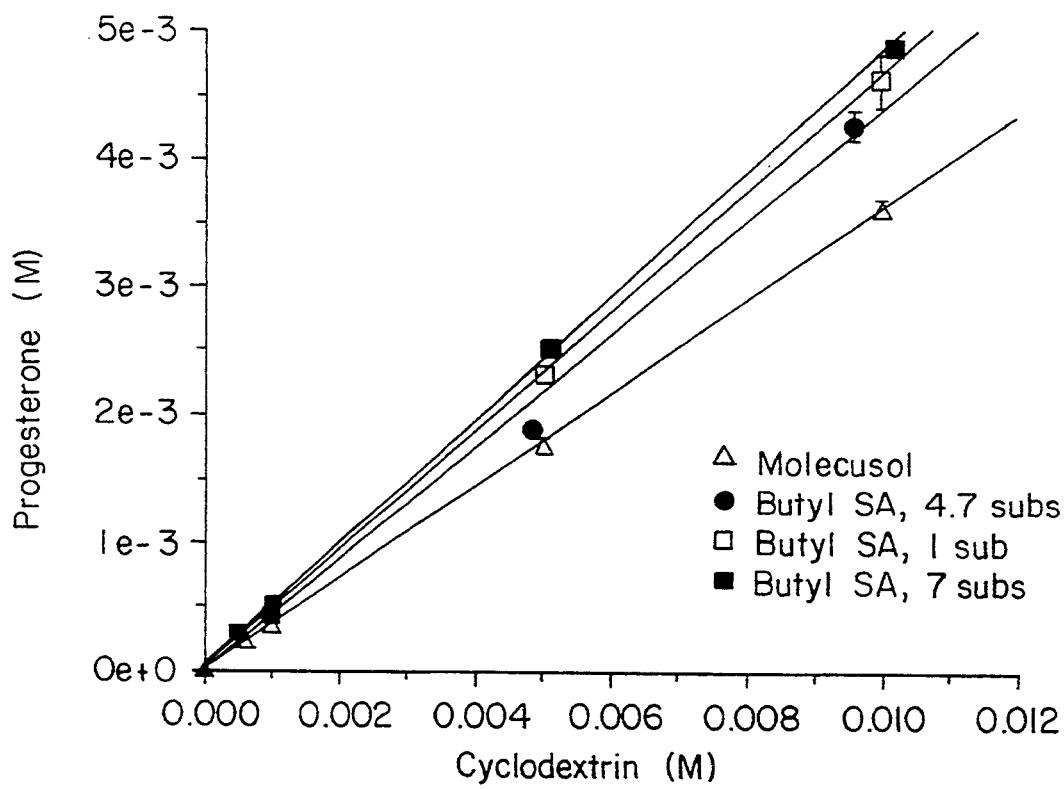
Figure 6:
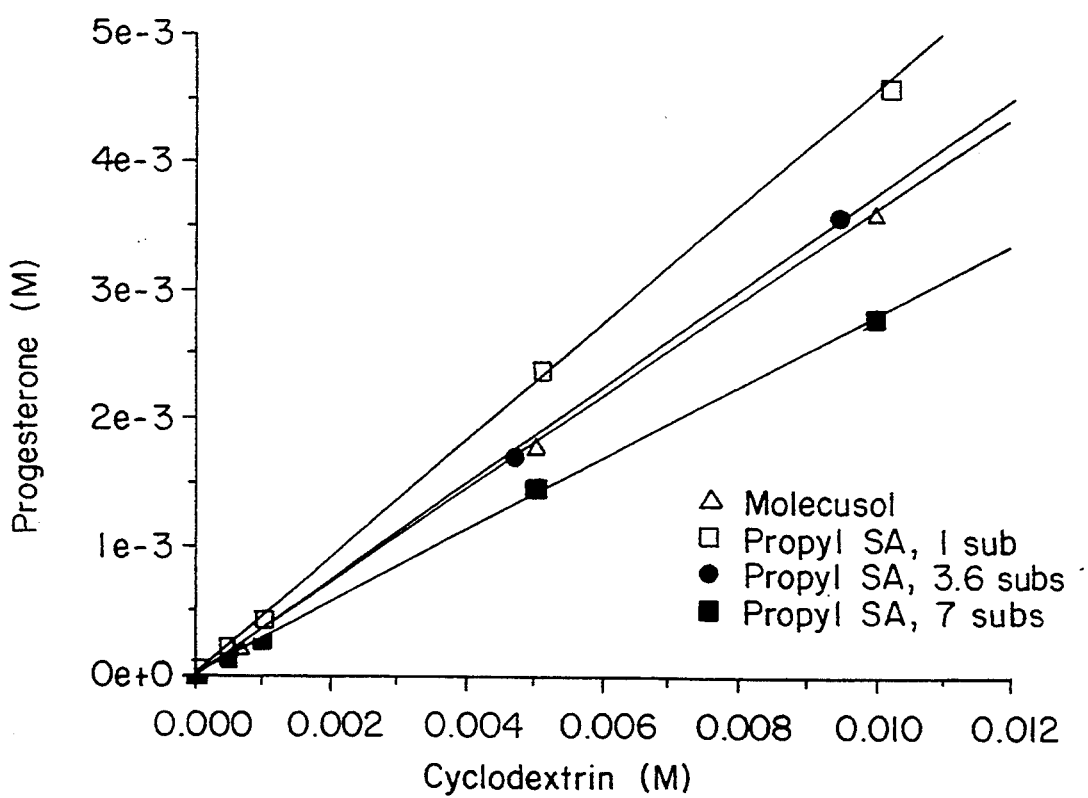
Figure 7:
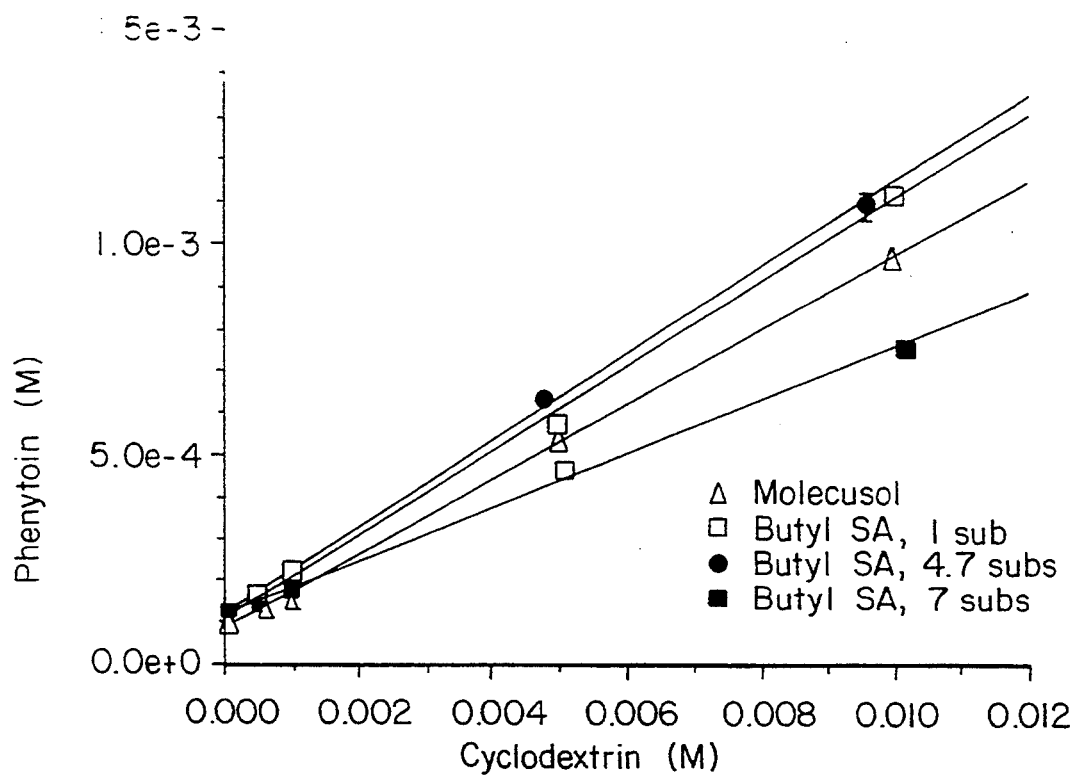
FIGS. 7, 8, 9 and 10 similarly show that with phenytoin and testosterone the sulfoalkyl cyclodextrin derivatives of the present invention possess notably greater association constants as compared to the hydroxypropyl cyclodextrin derivative.
Figure 8:
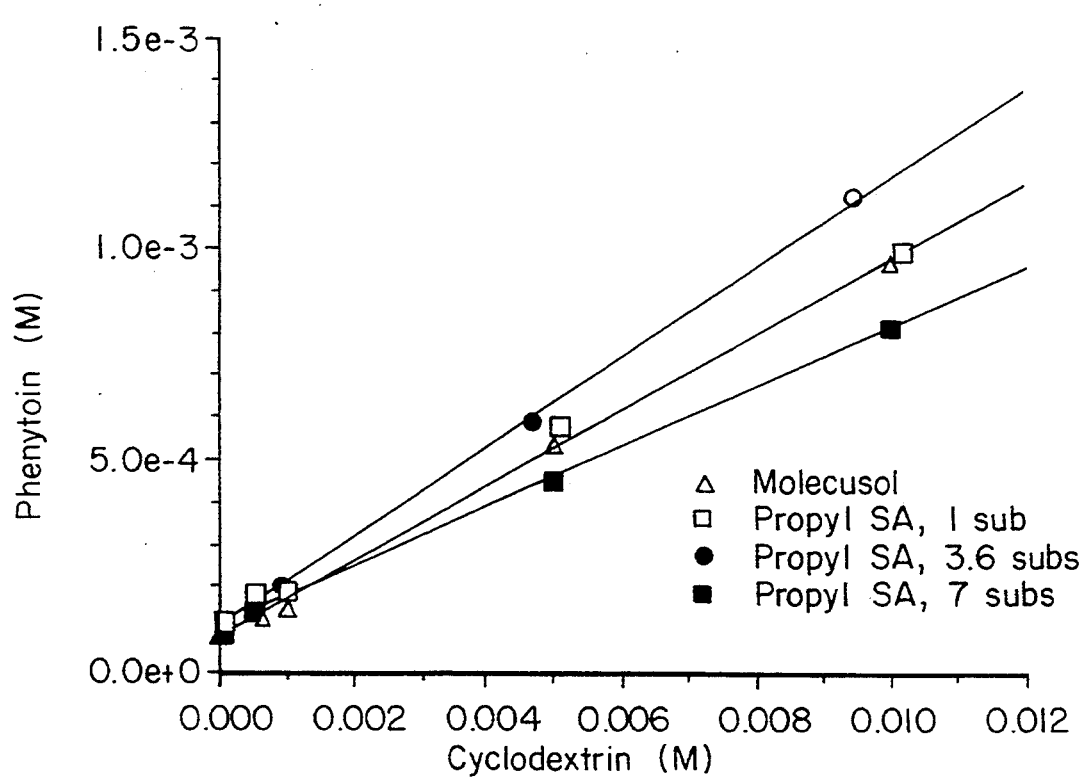
Figure 9:
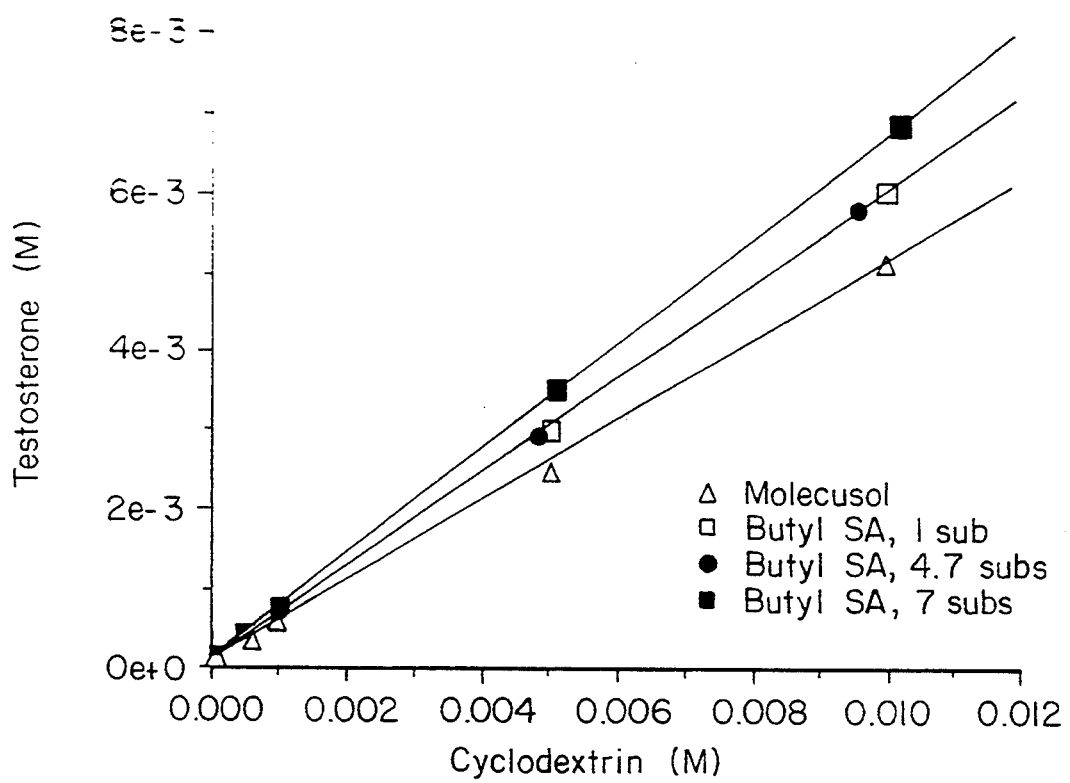
Figure 10:
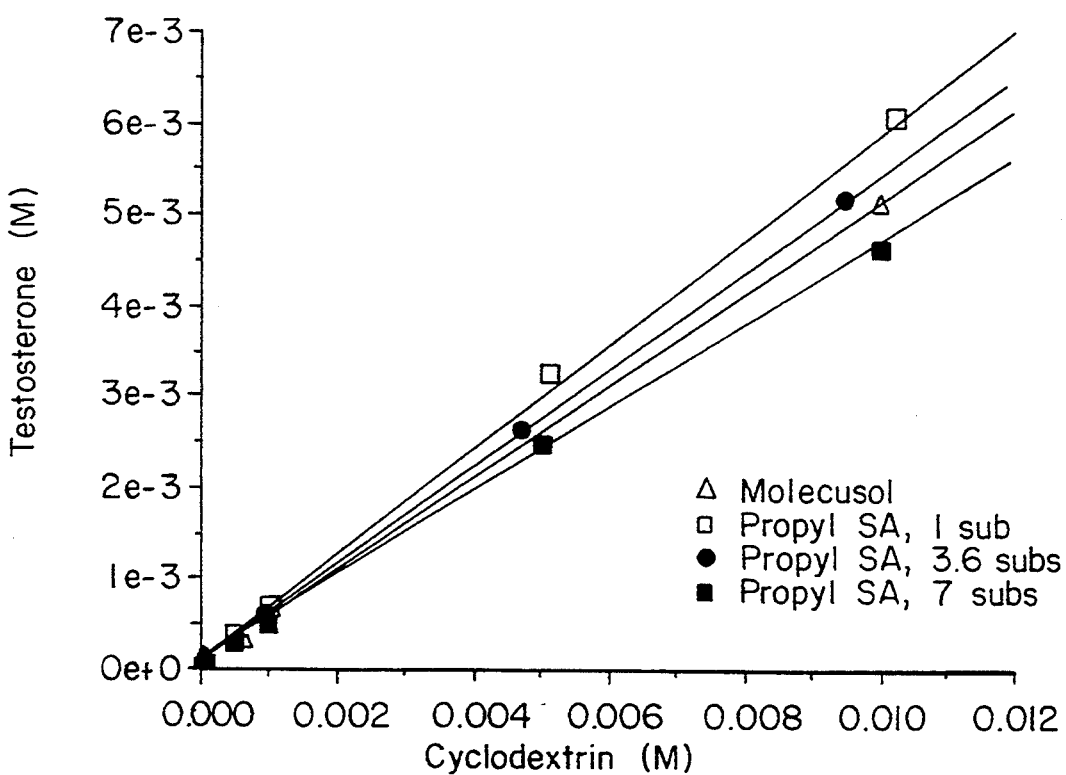

Similar results can be seen for progesterone (see Table 3 and FIGS. 5 and 6), phenytoin (see Table 4 and FIGS. 7 and 8), and testosterone (see Table 5 and FIGS. 9 and 10).

TABLE 5
TESTOSTERONE ASSOCIATION CONSTANTS

| | $K_{1:1}(M^{-1})$ |
|---|---|
| β-cyclodextrin | $1.78 \times 10^4$ |
| Molecusol (hydroxypropyl β-CD) | $1.16 \times 10^4$ |
| (1 sub)[1] | $1.64 \times 10^4$ |
| Sulfobutyl ether β-cyclodextrin | |
| (4.7 subs) | $1.82 \times 10^4$ |
| (7 subs) | $2.25 \times 10^4$ |
| Sulfopropyl ether β-cyclodextrin | |
| (1 sub) | $1.87 \times 10^4$ |
| (3.6 subs) | $1.43 \times 10^4$ |
| (7 subs) | $9.63 \times 10^3$ |

[1]No. of substituents per CD molecule

TABLE 6
PHENYTOIN ASSOCIATION CONSTANTS

| | $K_{1:1}(M^{-1})$ |
|---|---|
| β-cyclodextrin | $1.51 \times 10^3$ |
| Molecusol (hydroxypropyl β-CD) (1 sub)[1] | $1.07 \times 10^3$ |
| | $1.22 \times 10^3$ |
| Sulfobutyl ether β-cyclodextrin | |
| (4.7 subs) | $1.26 \times 10^3$ |
| (7 subs) | $7.56 \times 10^2$ |
| Sulfopropyl ether β-cyclodextrin | |
| (1 sub) | |
| (3.6 subs) | $1.31 \times 10^3$ |
| (7 subs) | $8.24 \times 10^2$ |

[1]No. of substituents per CD molecule

Studies on Oral Preparations:

As discussed above, oral formulations can tolerate higher amounts of β-cyclodextrin without compromising toxicity concerns. Useful tolerated levels of β-cyclodextrin, however, still depend upon a proper balancing of other characteristics, including particularly intrinsic aqueous solubility.

The maximum water solubility of any modified cyclodextrin dictates the limits of its usefulness in solubilizing drug substances. The greater the aqueous solubility the greater the potential for use of the cyclodextrin at high enough concentrations to solubilize all of the drug substance by formation of an inclusion complex. Table 6 shows the results of a comparison of the water solubility of various sulfoalkylether derivatives generated by the present invention which have been doped to contain <0.7 to 25% by weight residual β-cyclodextrin versus the water solubility of the derivatives generated by the method described in U.S. Pat. No. 3,426,011 to Parmerter which contain from 69–82% by weight residual β-cyclodextrin.

The results in Table 6 show that as the concentration of the residual β-cyclodextrin content increases from <1 weight percent up to 25 weight percent the aqueous solubility decreases. However, even at a content of 25% (wt/wt) residual β-cyclodextrin, the mixture of the sulfoalkyl ether derivatives exhibits water solubilities of 84 and 94 mg/mL for the sulfopropyl and sulfobutyl ether derivatives respectively. This means that the preparation according to the present invention containing as much as 25% by weight β-cyclodextrin would still exhibit a water solubility which was −1.5–2 times that of the corresponding Parmerter preparations.

TABLE 6
Effect of β-CD Content on Water Solubility
Comparison of Various Cyclodextrin Preparations

| CYCLODEXTRIN | % β-CD Content (wt/wt) (CZE)* | Water Solubility (mg/mL) |
|---|---|---|
| beta-Cyclodextrin (β-CD) Amaizo, β-CD | 100 | 19 |
| Sulfopropyl Ether Derivatives | | |
| Parmerter DAD-6-34 | 69 | 45 |
| Present Invention | | |
| DAD-6-40 + β-CD** | 25 | 84 |
| DAD-6-39-F*** | 7 | >700 |
| DAD-6-40-F*** | 8 | >700 |
| DAD-6-39-12**** | <0.7 | >700 |
| Sulfobutyl Ether Derivatives | | |
| Parmerter DAD-1-137 | 82 | 39 |
| Present Invention | | |
| DAD-6-17 + β-CD** | 25 | 94 |
| DAD-1-127 | <2 | >800 |
| DAD-6-12 | <2 | >800 |

TABLE 6-continued

Effect of β-CD Content on Water Solubility
Comparison of Various Cyclodextrin Preparations

| CYCLODEXTRIN | % β-CD Content (wt/wt) (CZE)* | Water Solubility (mg/mL) |
|---|---|---|
| DAD-6-17 | <2 | >800 |

Figure 11:
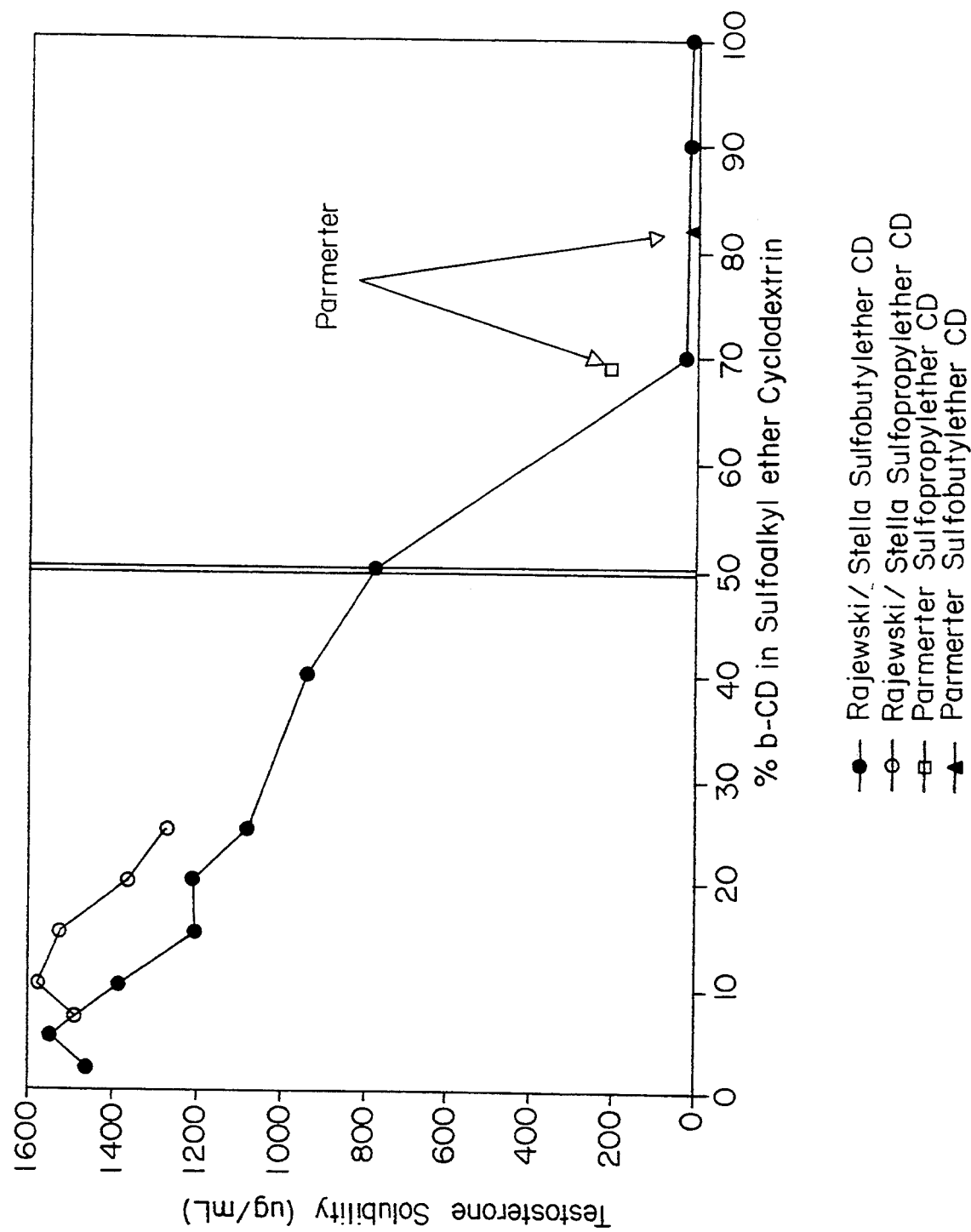
FIGS. 11, 12 and 13 show the results of solubility studies of testosterone, progesterone and naproxen with sulfoalkylether cyclodextrin derivatives of the present invention.
Figure 12:
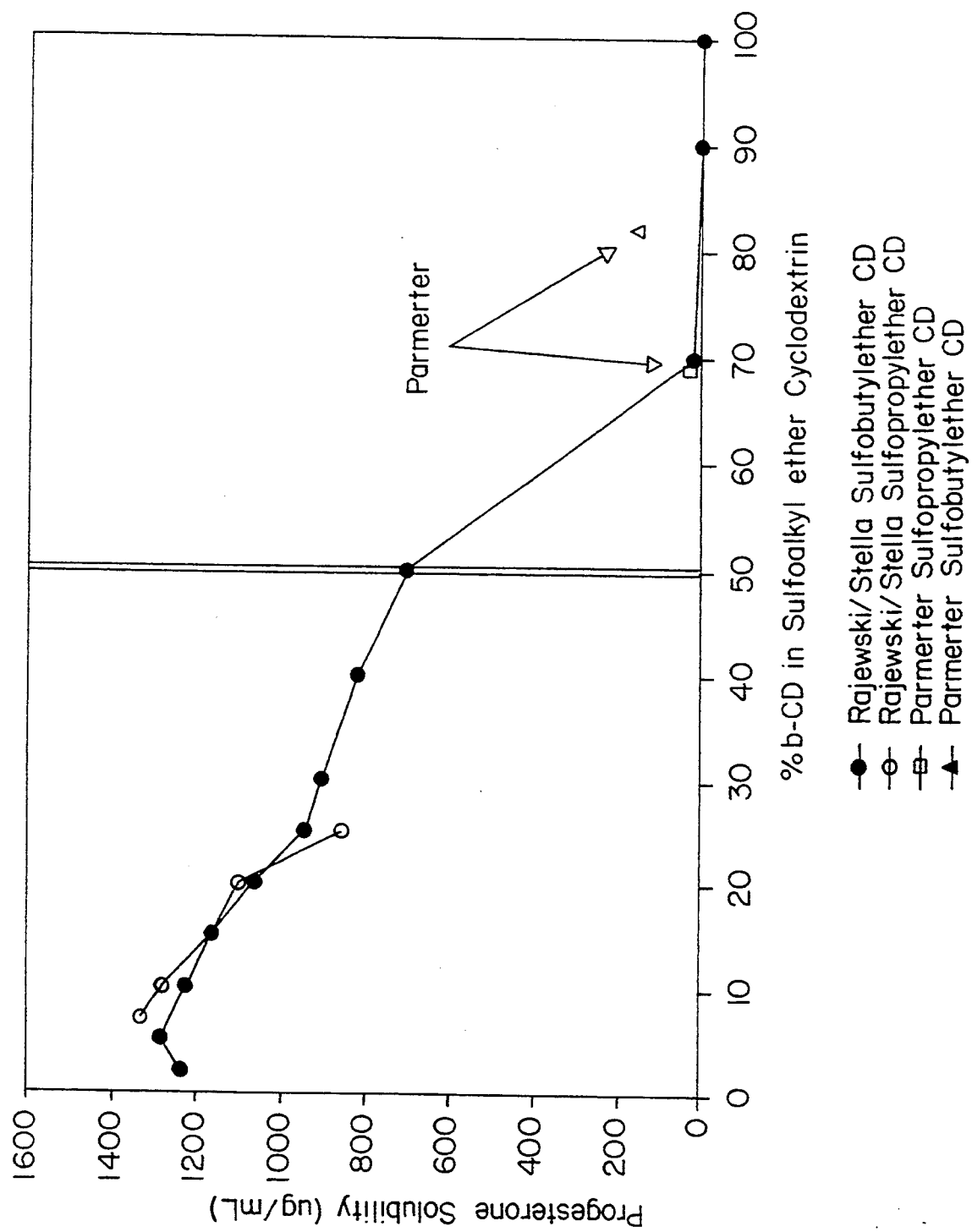
Figure 13:
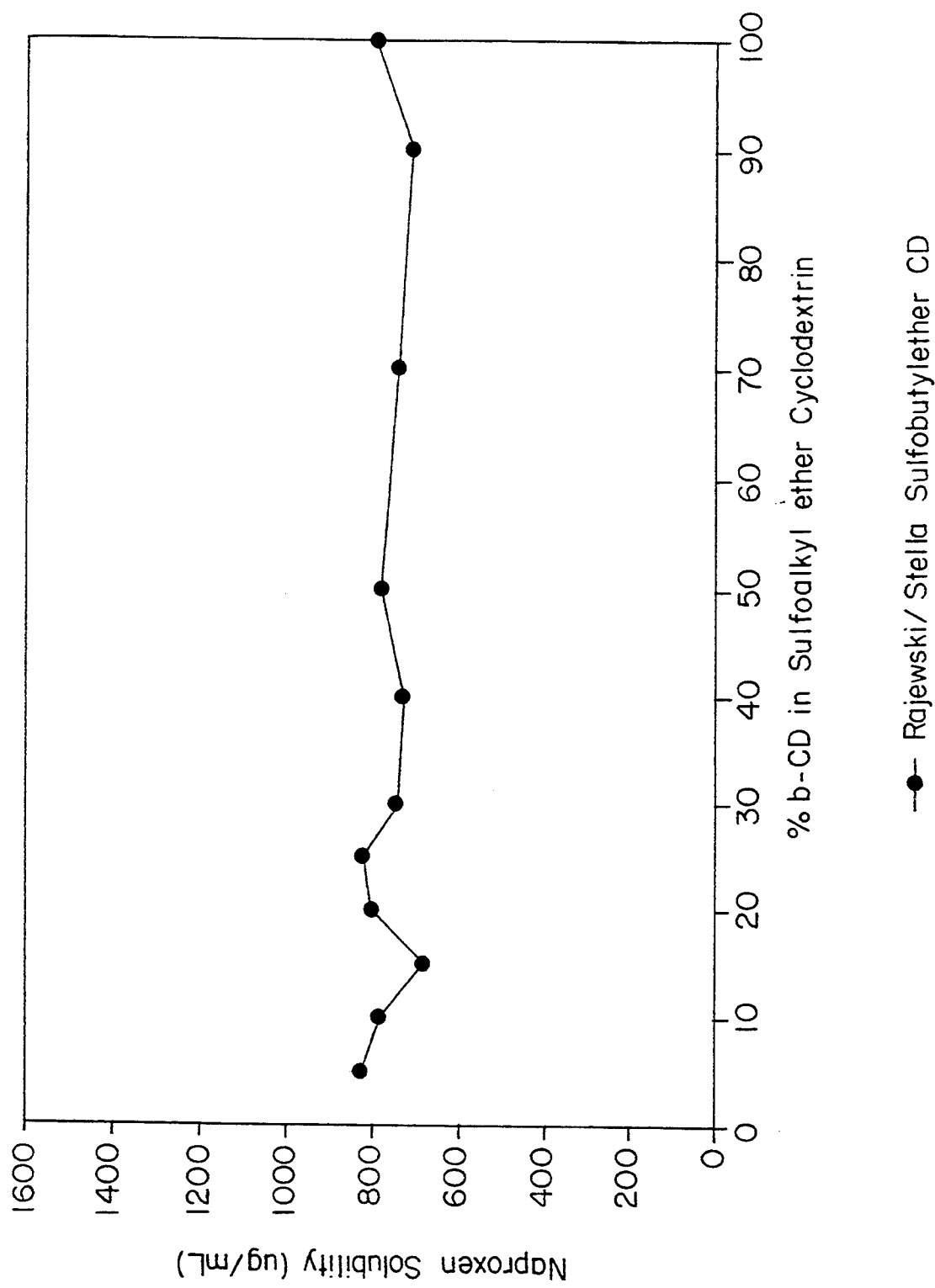

*Capillary Zone Electrophoresis
**Rajewski/Stella Preparation doped with beta-Cyclodextrin
***Rajewski/Stella Preparation prior to chromatographic step
****Rajewski/Stella Preparation after chromatographic step FIGS. 11–13 graphically show the solubility characteristics of several drugs with the derivatives of the present invention containing varying amounts of β-cyclodextrin. FIGS. 11 and 12 show the results of solubility studies with two different drugs, testosterone and progesterone, respectively. In both figures, solubility characteristics are plotted for the sulfobutyl ether and sulfopropyl ether derivatives of the present invention containing various amounts of β-cyclodextrin and also plotted are the sulfopropyl ether and sulfobutyl ether derivatives of Parmerter. The results in both studies show that the derivatives of the present invention exhibit much higher solubility as compared to the Parmerter derivatives. Even the composition containing the sulfobutyl ether derivative of the present invention with 50% β-cyclodextrin still showed much higher solubility as compared to the Parmerter compositions. The results also indicate, however, a rather dramatic decrease in solubility after the amount of β-cyclodextrin becomes greater than 50%.

FIG. 13 reports the results of solubility characteristics for naproxen for compositions of the sulfobutyl ether derivatives of the invention with various amounts of β-cyclodextrin. This study surprisingly showed that the solubility of naproxen was not as high as testosterone and progesterone at low levels of β-cyclodextrin, but also the solubility of the drug did not appear to significantly decrease with increasing amount of β-cyclodextrin. Nevertheless, the results in FIGS. 11 and 12 show that the solubility of some drugs does decrease with increasing amounts of β-cyclodextrin. For those drugs, compositions of the sulfoalkyl ether cyclodextrin derivatives of the present invention provide excellent drug solubility, even with up to 40–50% of β-cyclodextrin.

Obviously, numerous modifications and variations of the present invention are possible in light of the above teachings. It is therefore to be understood that within the scope of the appended claims, the invention may be practiced otherwise than as specifically described herein.

We claim:

1. A cyclodextrin derivative composition which comprises a cyclodextrin derivative of formula

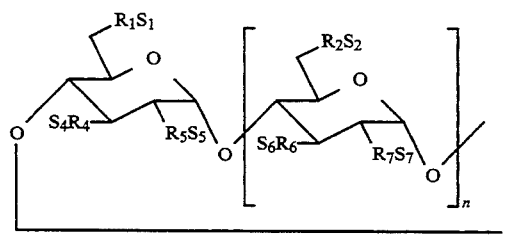

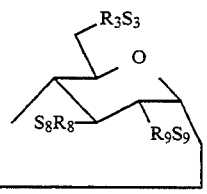

wherein:
n is 4, 5 or 6;
$R_1$, $R_2$, $R_3$, $R_4$, $R_5$, $R_6$, $R_7$, $R_8$ and $R_9$ are each, independently, $O^-$ or a $O\text{-}(C_{2\text{-}6}$ alkylene$)\text{-}SO_3^-$ group, and at least one of $R_1$ and $R_2$ is, independently, said $O\text{-}(C_{2\text{-}6}$ alkylene$)\text{-}SO_3^-$ group; and
$S_1$, $S_2$, $S_3$, $S_4$, $S_5$, $S_6$, $S_7$, $S_8$ and $S_9$ are each, independently, a pharmaceutically acceptable cation, and wherein said composition contains less than about 50% of underivatized cyclodextrin.

2. The composition of claim 1, wherein $R_1$, $R_2$ and $R_3$ are each, independently, said $O\text{-}(C_{2\text{-}6}$ alkylene$)\text{-}SO_3^-$ group.

3. The composition of claim 1, wherein $R_1$, $R_2$ and $R_3$ are each, independently a $O\text{-}(CH_2)_m\text{-}SO_3^-$ group, wherein m is 3 or 4.

4. The composition of claim 1, wherein:
at least one of $R_4$, $R_6$ and $R_8$ is, independently, said $O\text{-}(C_{2\text{-}6}\text{-alkylene})\text{-}SO_3^-$ group; and
$R_5$, $R_7$, and $R_9$ are all $O^-$.

5. The composition of claim 2, wherein:
at least one of $R_4$, $R_6$ and $R_8$ is, independently, said $O\text{-}(C_{2\text{-}6}\text{-alkylene})\text{-}SO_3^-$ group; and
$R_5$, $R_7$, and $R_9$ are all $O^-$.

6. The composition of claim 2, wherein:
$R_4$, $R_6$ and $R_8$ are each a $O\text{-}(C_{2\text{-}6}$ alkylene$)\text{-}SO_3^-$ group; and
$R_5$, $R_7$, and $R_9$ are all $O^-$.

7. The composition according to claim 1, wherein n is 5.

8. The composition according to claim 7, wherein said $C_{2\text{-}6}$ alkylene is a $C_3$ alkylene.

9. The composition according to claim 7, wherein said $C_{2\text{-}6}$ is a $C_4$ alkylene.

10. The composition according to claim 8, wherein said cyclodextrin derivatives in said composition contain an average of about one $O\text{-}(C_2\text{-}C_6$ alkylene$)\text{-}SO_3^-$ group per cyclodextrin molecule.

11. The composition according to claim 8, wherein said cyclodextrin derivatives in said composition contain an average of about 3.6 $O\text{-}(C_2\text{-}C_6$ alkylene$)\text{-}SO_3^-$ group per cyclodextrin molecule.

12. The composition according to claim 8, wherein said cyclodextrin derivatives in said composition contain an average of about 7 $O\text{-}(C_2\text{-}C_6$ alkylene$)$ -$SO_3^-$ group per cyclodextrin molecule.

13. The composition according to claim 9, wherein said cyclodextrin derivatives in said composition contain an average of about one $O\text{-}(C_2\text{-}C_6$ alkylene$)\text{-}SO_3^-$ group per cyclodextrin molecule.

14. The composition according to claim 9, wherein said cyclodextrin derivatives in said composition contain an average of about 4.7 $O\text{-}(C_2\text{-}C_6$ alkylene$)\text{-}SO_3^-$ group per cyclodextrin molecule.

15. The composition according to claim 9, wherein said cyclodextrin derivatives in said composition contain an average of about 7 $O\text{-}(C_2\text{-}C_6$ alkylene$)\text{-}SO_3^-$ group per cyclodextrin molecule.

16. The composition according to claim 1, wherein said composition contains less than 40% underivatized cyclodextrin.

17. The composition according to claim 7, wherein said composition contains less than 40% underivatized cyclodextrin.

18. The composition according to claim 8, wherein said composition contains less than 40% β-cyclodextrin.

19. The composition according to claim 9, wherein said composition contains less than 40% β-cyclodextrin.

20. The composition according to claim 16, wherein said composition contains less than 25% β-cyclodextrin.

21. The composition according to claim 17, wherein said composition contains less than 25% underivatized cyclodextrin.

22. The composition according to claim 8, wherein said composition contains less than 25% underivatized cyclodextrin.

23. The composition according to claim 9, wherein said composition contains less than 25% β-cyclodextrin.

24. A composition comprising a drug complexed to a cyclodextrin derivative of formula (2):

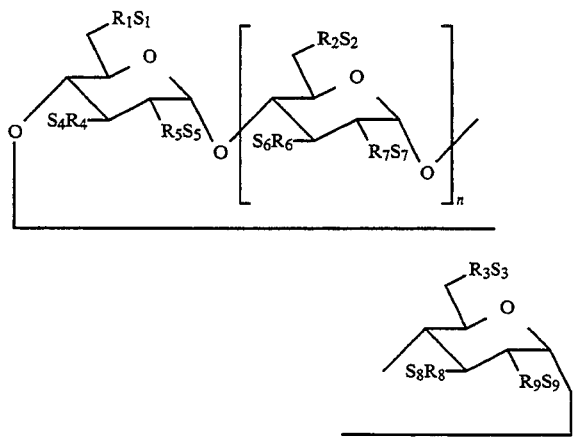

wherein:
n is 4, 5 or 6;
$R_1$, $R_2$, $R_3$, $R_4$, $R_5$, $R_6$, $R_7$, $R_8$ and $R_9$ are each independently $O^-$ or a $O\text{-}(C_{2\text{-}6}\text{ alkylene})\text{-}SO_3^-$ group, and at least one of $R_1$ and $R_2$ is, independently, said $O\text{-}(C_{2\text{-}6}\text{ alkylene})\text{-}SO_3^-$ group; and
$S_1$ to $S_9$ are each, independently, a pharmaceutically acceptable cation;
wherein said composition contains not more than about 50 wt. % of underivatized cyclodextrin.

25. The composition of claim 24, wherein $R_1$, $R_2$ and $R_3$ are each, independently, said $O\text{-}(C_{2\text{-}6}\text{ alkylene})\text{-}S_3^-$ group.

26. The composition of claim 24, wherein:
at least one of $R_4$, $R_6$ and $R_8$ is, independently, said $O\text{-}(C_{2\text{-}6}\text{-alkylene})\text{-}SO_3^-$ group; and
$R_5$, $R_7$, and $R_9$ are all $O^-$.

27. The composition of claim 25, wherein:
at least one of $R_4$, $R_6$ and $R_8$ is, independently, said $O\text{-}(C_{2\text{-}6}\text{-alkylene})\text{-}SO_3^-$ group; and
$R_5$, $R_7$, and $R_9$ are all $O^-$.

28. The composition of claim 27, wherein $R_4$, $R_6$ and $R_8$ are each, independently, said $O\text{-}(C_{2\text{-}6}\text{ alkylene})\text{-}SO_3^-$ group.

29. The composition of claim 24, wherein said drug is one member selected from the group consisting of amobarbital, ampicillin, aspirin, beclomethasone, benzocaine, benzodiazepines, betamethasone, chlorambucil, chloramphenicol, chlorpromazine, clofibrate, coenzyme A, cortisone, cortisone acetate, cyclobarbital, dexamethasone, dexamethasone acetate, diazepam, digitoxin, digoxin, estradiol, 5-fluorouracil, flurbiprofen, griseofulvin, hydrocortisone, hydrocortisone acetate, ibuprofen, indomethanin, ketoprofen, methicillin, metronidazole, mitomycin, nitrazepam, nitroglycerin, penicillin, pentobarbital, phenobarbital, phenobarbitone, phenyltoin, prednisolone, prednisolone acetate, progesterone, prostaglandin A series, prostaglandin B series, prostaglandin E series, prostaglandin F series, reserpine, sulfaceatamide sodium, testosterone, vitamin A, vitamin D3, vitamin E, vitamin K3, and warfarin.

30. The composition according to claim 24, wherein n is 5.

31. The composition according to claim 30, wherein said $C_{2\text{-}6}$ alkylene is a $C_3$ alkylene.

32. The composition according to claim 30, wherein said $C_{2\text{-}6}$ is a $C_4$ alkylene.

33. The composition according to claim 31, wherein said cyclodextrin derivatives in said composition contain an average of about 1, 3.6 or 7 $O\text{-}(C_2\text{-}C_6\text{ alkylene})\text{-}SO_3^-$ groups per cyclodextrin molecule.

34. The composition according to claim 32, wherein said cyclodextrin derivatives in said composition contain an average of about 1, 4.7 or 7 $O\text{-}(C_2\text{-}C_6\text{ alkylene})\text{-}SO_3^-$ groups per cyclodextrin molecule.

35. The composition according to claim 24, wherein said composition contains less than 40% β-cyclodextrin.

36. The composition according to claim 30, wherein said composition contains less than 40% β-cyclodextrin.

37. The composition according to claim 31, wherein said composition contains less than 40% β-cyclodextrin.

38. The composition according to claim 32, wherein said composition contains less than 40% β-cyclodextrin.

39. The composition according to claim 33 wherein said composition contains less than 40% β-cyclodextrin.

40. The composition according to claim 34, wherein said composition contains less than 40% β-cyclodextrin.

41. The composition according to claim 35, wherein said composition contains less than 25% β-cyclodextrin.

42. The composition according to claim 36, wherein said composition contains less than 25% β-cyclodextrin.

43. The composition according to claim 37, wherein said composition contains less than 25% β-cyclodextrin.

44. The composition according to claim 38, wherein said composition contains less than 25% β-cyclodextrin.

45. The composition according to claim 39, wherein said composition contains less than 25% β-cyclodextrin.

46. The composition according to claim 40 wherein said composition contains less than 25% β-cyclodextrin.

47. A pharmaceutical composition for oral administration comprising a pharmaceutically, orally suitable carrier and a clathrate complex comprising a drug complexed to a cyclodextrin derivative of formula (2):

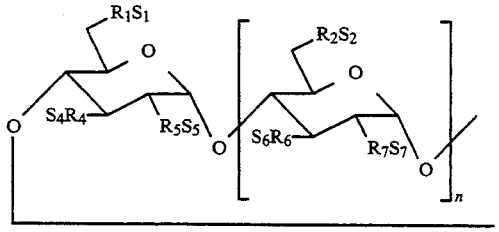

-continued

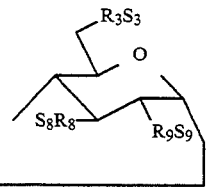

wherein:
n is 4, 5 or 6;
$R_1$, $R_2$, $R_3$, $R_4$, $R_5$, $R_6$, $R_7$, $R_8$ and $R_9$ are each independently $O^-$ or a $O$-($C_{2-6}$ alkylene)-$SO_3^-$ group, and at least one of $R_1$ and $R_2$ is, independently, said $O$-($C_{2-6}$ alkylene)-$SO_3^-$ group; and
$S_1$ to $S_9$ are each, independently, a pharmaceutically acceptable cation;
wherein said composition contains not more than 50 wt. % of underivatized cyclodextrin.

* * * * *

UNITED STATES PATENT AND TRADEMARK OFFICE
CERTIFICATE OF CORRECTION

PATENT NO. : 5,376,645
DATED      : December 27, 1994
INVENTOR(S): Valentino J. STELLA et al.

It is certified that error appears in the above-identified patent and that said Letters Patent is hereby corrected as shown below:

Column 1, Line 9, after "BACKGROUND OF THE INVENTION" insert the following:

--This invention was made with government support under N01-CM-67912 and N01-CM-97546 awarded by the National Institutes of Health. The government has certain rights in the invention.--

Signed and Sealed this

Nineteenth Day of May, 1998

Attest:

Attesting Officer

BRUCE LEHMAN

Commissioner of Patents and Trademarks

UNITED STATES PATENT AND TRADEMARK OFFICE
CERTIFICATE OF CORRECTION

PATENT NO. : 5,376,645
DATED : December 27, 1994
INVENTOR(S) : Valentino J. STELLA et al.

It is certified that error appears in the above-identified patent and that said Letters Patent is hereby corrected as shown below:

On the title page, Item [*], "July 28,2008" should read --January 23,2010--.

Signed and Sealed this

Twenty-ninth Day of June, 1999

*Attest:*

Q. TODD DICKINSON

*Attesting Officer*     *Acting Commissioner of Patents and Trademarks*